United States Patent [19]

Najafi et al.

[11] Patent Number: 5,314,458
[45] Date of Patent: May 24, 1994

[54] SINGLE CHANNEL MICROSTIMULATOR

[75] Inventors: Khalil Najafi; Kensall D. Wise, both of Ann Arbor, Mich.

[73] Assignee: University of Michigan, Ann Arbor, Mich.

[21] Appl. No.: 66,925

[22] Filed: May 24, 1993

Related U.S. Application Data

[63] Continuation of Ser. No. 532,271, Jun. 1, 1990, abandoned.

[51] Int. Cl.$^5$ .............................................. A61N 1/18
[52] U.S. Cl. ................................. 607/116; 607/148; 607/60; 607/61; 607/2; 128/903; 623/901; 623/24
[58] Field of Search ............ 607/116, 115, 2, 60, 607/61, 148, 41, 40, 42, 53; 128/903, 642; 623/11, 24, 901

[56] References Cited

U.S. PATENT DOCUMENTS

| | | | |
|---|---|---|---|
| 3,662,758 | 5/1972 | Glover | 128/903 |
| 3,727,616 | 4/1973 | Lenzkes | 128/419 E |
| 4,102,344 | 7/1978 | Conway et al. | 128/419 E |
| 4,494,950 | 1/1985 | Fischell | 128/903 |
| 4,524,774 | 6/1985 | Hildebrandt | 128/903 |
| 4,561,443 | 12/1985 | Hogrefe et al. | 128/903 |
| 4,628,933 | 12/1986 | Michelson | 128/419 R |
| 4,736,752 | 4/1988 | Munck et al. | 128/798 |
| 4,741,339 | 5/1988 | Harrison et al. | 128/903 |
| 4,837,049 | 6/1989 | Byers et al. | 128/784 |
| 4,932,405 | 6/1990 | Peeters et al. | 128/419 R |
| 5,070,535 | 12/1991 | Hochmair et al. | 128/903 |
| 5,215,088 | 6/1993 | Normann et al. | 607/116 |

OTHER PUBLICATIONS

Meindl et al., "Implantable Telemetry in Biomedical Research," IEEE vol. RME-31, No. 12, Dec. 1984.
Ko et al., "RF-Powered Cage System for Implant Biotelemetry," IEEE vol. BME-27, No. 8, Aug. 1980.

Primary Examiner—William E. Kamm
Assistant Examiner—Kennedy J. Schaetzle
Attorney, Agent, or Firm—Rohm & Monsanto

[57] ABSTRACT

An implantable microstimulator system employs a miniature ferrite-cored coil contained with an hermetically sealed housing to receive control signals and operating power from an RF telemetry system. The tiny coil receives the electromagnetic energy which is transmitted from a non-implantable transmitter which generates a code-modulated carrier. Demodulator circuitry in the implantable microcircuit is employed to extract the control information, while applying the electromagnetic energy to power the electronic circuitry therein and charge a capacitor which will provide the electrical stimulation to the living being. The electrical stimulation is delivered by a stimulating electrode which has a waffle-like configuration whereby a plurality of iridium oxide electrode pads, coupled in parallel, so as to be characterized by a long effective edge distance, transfer the stimulating charge. The electrical components of the implantable microstimulator are contained within an hermetically sealed housing formed of a glass capsule which is electrostatically bonded to a silicon substrate.

12 Claims, 10 Drawing Sheets

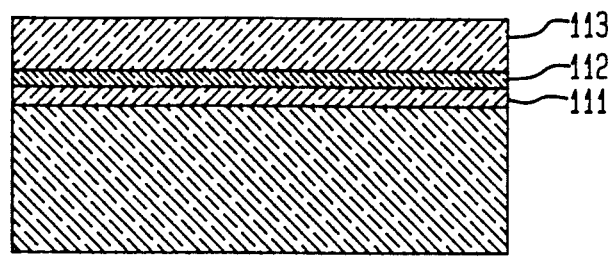
FIG. 11A
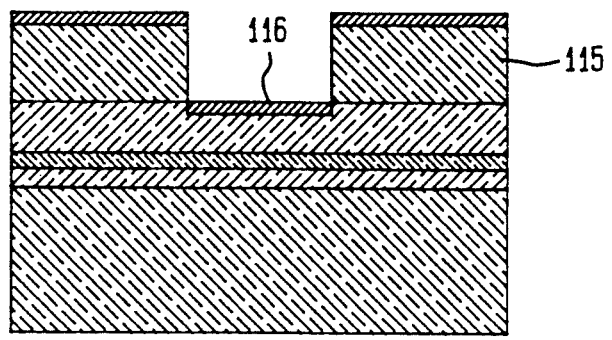
FIG. 11B
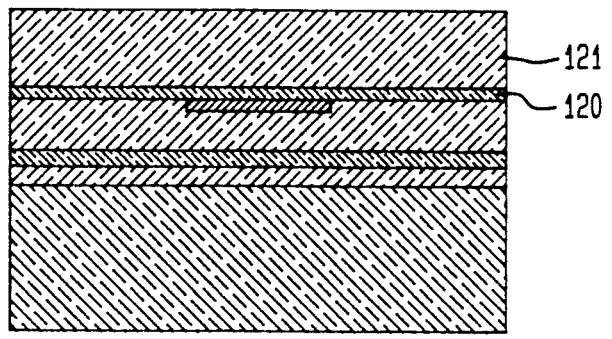
FIG. 11C
FIG. 11D
FIG. 11E
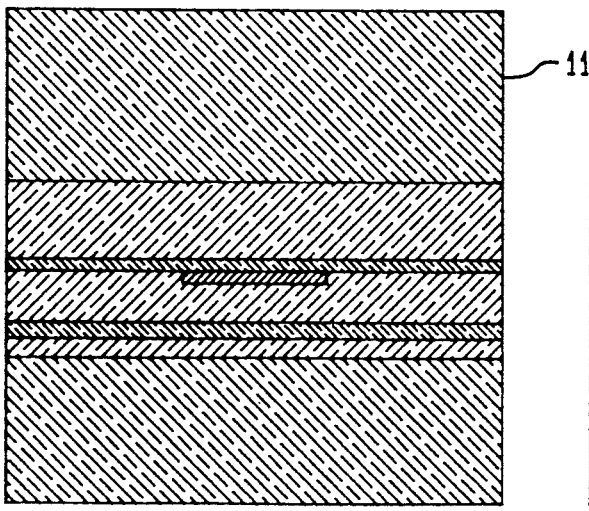
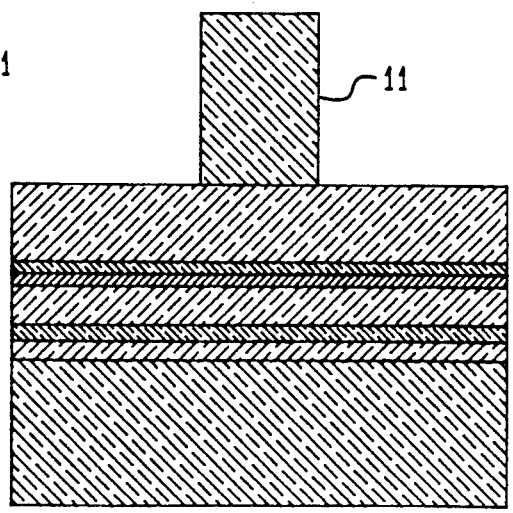

SINGLE CHANNEL MICROSTIMULATOR

This invention was made with government support under Contract NO1NS82312 awarded by the National Institutes of Health. The government has certain rights in the invention.

This application is a continuation of application Ser. No. 07/532,271 filed Jun. 1, 1990, now abandoned.

BACKGROUND OF THE INVENTION

This invention relates generally to prosthetic devices and systems, and more particularly to an implantable microstimulator which receives power and coded information via a radio frequency telemetry system.

The application of electrical stimulation to a living being is one of the primary techniques used in restoring function to the functionally-impaired. Additionally, such electrical stimulation has found application in the control of pain and may be useful in certain cases for the restoration of sight. There is presently in the art a great need for new and improved tools and techniques useful in the restoration of controllable function to patients having a wide variety of functional disorders. For example, neuromuscular electrical stimulation has been used to provide controllable hand movements in the upper extremity of spinal cord injury patients. Other important uses include the providing of respiration control to tetraplegic patients with respiratory paralysis; by stimulating the phrenic nerve, to void the bladder of paralyzed patients; and to treat urinary and anal incontinence.

It is, of course, of utmost importance that implantable tissue stimulation systems be designed to withstand long-term exposure to body fluids. Additionally, such electrical stimulators must be able to provide sufficient charge to effect the tissue stimulation, and to deliver the charge into the tissue reliably. It is further required that the stimulators be small, low in cost, reliable, and provide results which are reproducible.

Presently, most stimulators utilize discrete wiring to form stimulation electrodes, and therefore require relatively large (on the order of a few centimeters) packages to house the electronic circuitry and the power sources, which may include batteries and/or an antenna. There clearly is a need for improvements to electrical stimulator systems, in terms of both package dimensions and operating characteristics.

One of the most challenging areas in the field of implantable transducers has been the transfer of data and power into and out of the body of the living being. Although hard-wired systems have been generally used, they impose many problems on the overall structure in terms of:

(1) hermetic encapsulation at the entrance and exit points of the output leads;

(2) tethering effects due to the output leads;

(3) infection at the sight of the wires breaking the skin barrier; and (4) low yield and labor intensive assembly and packaging.

In certain applications, the transmission of power and data using radio frequency telemetry has been employed with success. The known systems, however, employ implantable antennae that typically are required to be quite large in order to generate the requisite amount of power. Not only is there a need to reduce the size of the antenna, which may be on the order of several centimeters, but there is additionally the need to eliminate all external leads to the implant.

It is, therefore, an object of this invention to provide an implantable stimulator arrangement which is economical to manufacture and does not require external leads to obtain operating power and information.

It is another object of this invention to provide a microstimulator arrangement which can receive power and information from a radio frequency signal.

It is also an object of this invention to provide an electrical stimulator arrangement which can easily be implanted into a living being.

It is further object of this invention to provide an implantable stimulator system having an electrode which reliably can deliver high stimulation currents to a living being.

It is additionally an object of this invention to provide an implantable electrical stimulator system which avoids the problem of tethering due to the presence of output electrical leads.

It is yet a further object of this invention to provide a microstimulator arrangement which is hermetically encapsulated, and wherein the encapsulation is not compromised at the entrance and exit points of the output (electrode) leads.

It is also another object of this invention to provide an electrical stimulator assembly which avoids the problem of infection at the site where wires break through the skin barrier.

It is yet an additional object of this invention to provide an implantable microstimulator for neuromuscular stimulation which is easily and economically manufactured, achieving high yield and without labor-intensive assembly and/or packaging.

SUMMARY OF THE INVENTION

The foregoing and other objects are achieved by this invention which provides an electrical stimulator system for implantation into the body of a living being. In accordance with the invention, the electrical stimulator system is provided with a non-implantable portion which is itself provided with a code generator for producing a coded information and a transmitter for transmitting an electromagnetic energy signal which contains the coded information. The electrical stimulator is further provided with an implantable portion which is provided with a receiver for receiving the electromagnetic energy and a code detector which is coupled to the receiver for detecting the coded information contained in the electromagnetic energy signal. The implantable portion of the electrical stimulator is further provided with an energy storage element, illustratively in the form of a capacitor, for storing electrical energy obtained from the electromagnetic energy signal. This stored energy is that which is applied to a stimulator electrode which is coupled to the energy storage element and the internal tissue of the living being.

In certain embodiments of the invention, it is desirable to provided a reference electrode which communicates with the tissue of the living being. The reference electrode may be coupled to the energy storage element, as is the stimulator electrode, and serves to provide an electrical point of reference for the stimulation energy supplied by the system.

Power and information, such as address information, is supplied via a radio frequency telemetry link to a receiver coil in the implantable portion of the electrical stimulator system. The receiver coil thereby forms a receiving antenna which supplies electrical energy to the stimulator system, as well as coded information. The electrical energy and the information is obtained from the transmitter, which is provided with a transmitter coil adapted to surround the receiver coil during transmission of the electromagnetic signal.

Predetermined portions of the implantable portion of the electrical stimulator are encapsulated within an hermetically sealed housing. The housing may contain within it the receiver coil which receives the electromagnetic communication from the transmitter. In certain embodiments, certain ones of the components of the implantable portion of the stimulator system are formed on a silicon substrate, by application of integrated circuit fabrication techniques. The housing is installed on the silicon substrate so as to contain therewithin the predetermined components of the stimulator system. In one highly advantageous embodiment of the invention, the hermetic housing is installed on the silicon substrate by an electrostatic bonding technique. However, the stimulator electrode, and the reference electrode of certain embodiments, are arranged on the silicon substrate, but outside of the hermetically sealed housing. Such electrodes are arranged to be in electrical communication with the components contained within the housing via thin metallic conductors. In a highly advantageous embodiment, the thin metallic conductors have a thickness on the order of approximately 500 Å, and are applied using low pressure chemical vapor deposition dielectrics. The hermetically sealed housing, which may be in the form of a glass capsule, is bonded directly over the conductor-dielectric combination. Since the interconnecting lead is sandwiched between deposited dielectric layers, excessive electrical leakage is prevented.

As indicated, the implantable portion of the electrical stimulator receives both, power and information, from the transmitter of the non-implantable portion. In a preferred embodiment, the implantable portion is provided with a demodulator arrangement which separates the incoming radio-frequency signal into information and carrier components. The information is provided to code detector circuitry for controlling the operation of the electrical stimulator, and the carrier energy is applied to the energy storage element, which may be a capacitor, for providing circuit power and stimulation charge.

One highly advantageous aspect of the present invention includes a novel electrode configuration for delivering the stimulator charge to the tissue of the living being. Delamination of the electrode from the silicon substrate is avoided by an electrode configuration wherein the total length of electrode edges is increased to reduce the current density during application of the charge at the electrode edge. In one further highly advantageous embodiment of the invention, the electrode is formed of a continuous layer of metallic conductor on which is deposited a dielectric layer having a plurality of openings therethrough. In one specific embodiment, the resulting openings in the dielectric layer are occupied by a stimulator electrode layer, which may be formed of iridium oxide. Thus, the overall electrode has a waffle-like appearance.

In accordance with a further aspect of the invention, an implantable prosthetic device is provided with an arrangement for delivering electrical power and information via a radio-frequency antenna in the form of a miniature receiver coil.

In a specific illustrative embodiment of this further aspect of the invention, the miniature receiver coil is formed of approximately 180 turns of 40 gauge wire. This results in a diameter which is less than 1.7 mm for the coil, and therefore, it can be contained within the hermetically sealed housing.

In operation, the transmitter coil is arranged coaxially with the receiver coil. In this manner, sufficient power is produced at the receiver coil to provide a supply for all of the electronic circuitry on the microstimulator, as well as the stimulation charge which is delivered to the living being.

BRIEF DESCRIPTION OF THE DRAWING

Comprehension of the invention is facilitated by reading the following detailed description, in conjunction with the annexed drawing, in which:

FIGS. 11A-11E show a schematic representation which illustrates the sequence of steps employed in the formation of leads for conducting electrical energy from within the hermetic seal to the electrodes;

DETAILED DESCRIPTION

Figure 1:
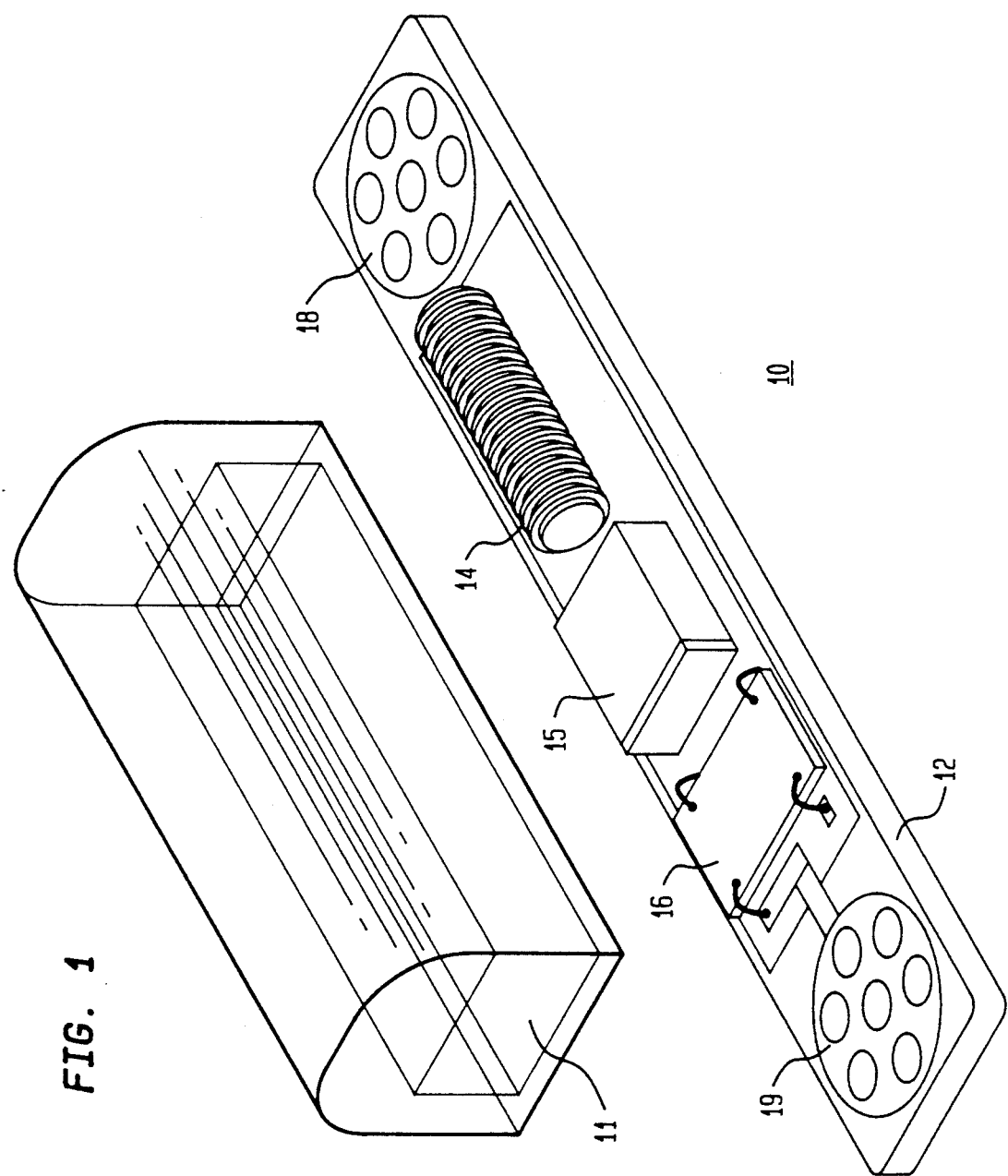
FIG. 1 is an isometric representation of an illustrative embodiment of the invention showing the various components of the implantable portion of a stimulator system constructed in accordance with the principles of the invention, with the glass capsule package removed.

FIG. 1 is a partially exploded isometric representation of a specific illustrative embodiment of an implantable single-channel microstimulator 10. Microstimulator 10 is entirely implantable in the body of a living being (not shown) and is provided with a glass capsule package 11 which is intended to be installed over a silicon substrate 12. Silicon substrate 12 has a receiving coil 14, a charge storage capacitor 15 and an integrated circuit chip 16 installed thereon. These structural elements, as will be described hereinbelow, are accommodated within glass capsule package 11 which forms an hermetic seal with silicon substrate 12. The silicon substrate is further provided with a reference electrode 18 and a stimulating electrode 19.

Figure 2:
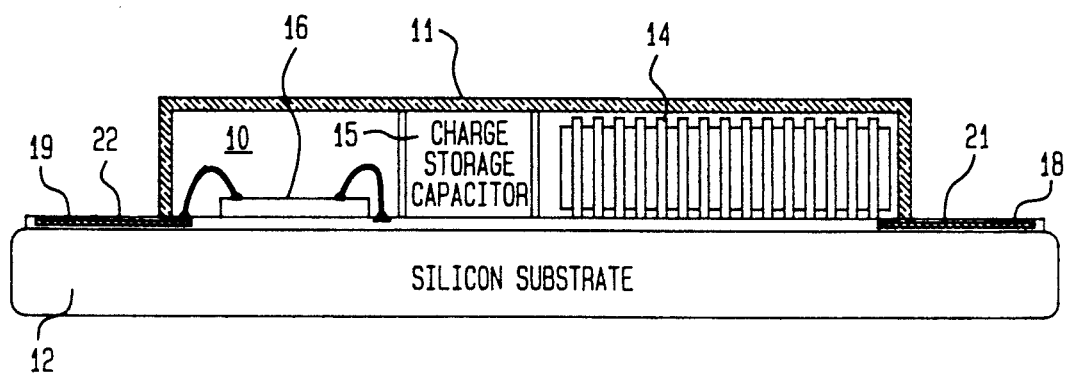
FIG. 2 is a cross-sectional side view of the embodiment of FIG. 1 showing the arrangement of components with the glass capsule package installed.

FIG. 2 is a partially cross-sectioned side view of the specific illustrative embodiment of microstimulator 10 shown in FIG. 1. Accordingly, corresponding elements of structure are similarly designated. As indicated, FIG. 2 shows the glass capsule package bonded to silicon substrate 12 to form a sealed interior chamber where receiver coil 14, storage capacitor 15, and integrated circuit chip 16 are disposed. However, electrical communication is effected between the electronic circuit elements contained under glass capsule package 11 and stimulating and reference electrodes by respectively associated conductor elements 21 and 22. The conductor elements will be described in detail hereinbelow.

In the practice of the invention, it is required that the overall system, including the implantable microstimulator of FIGS. 1 and 2 and an external transmitter (not shown in these figures) satisfy the requirements set forth in Table 1.

TABLE 1

| REQUIREMENTS FOR THE MICROSTIMULATOR SYSTEM | |
|---|---|
| IMPLANTABLE STIMULATOR PORTION | |
| Size: | |
| Diameter: | $\leq 1.7$ mm |
| Length: | $\leq 9$ mm |
| Biphastic Stimulation: | |
| First Phase: | |
| Duration: | $T_S = 0\text{--}200$ μsec. |
| Charge Delivery: | $Q = 2$ μC into Loads $R_L \leq 800$ Ohms |
| Second Phase: | Guarantee Charge Balance in $T \leq 25$ msec |
| Stimulation Rate: | 0–40 Hz |
| Operational Lifetime: | In Vivo For One Year at 37° C. |
| Addressability: | Up to 32 Stimulators Driven Using a Single Transmitter |
| TRANSMITTER PORTION | |
| Range: | |
| Diameter: | 9 cm |
| Depth: | 2 cm |
| Misalignment: | 10° |

Microstimulator 10 is powered and controlled using a radio-frequency inductive link, as will be described herein. The control signals are coded and sent into the stimulator by gating the RF current on and off. In accordance with Table 1, the output stage should deliver 2 μC of charge into loads greater than 800 ohms in a period of 200 μsec. This translates into a constant current of 10 mA during the stimulation phase. The voltage developed is therefore 8 V. In order to deliver this amount of charge in the specified period of time, the charge storage capacitor should have a size greater than 0.25 μF. After stimulation and in order to perform charge balance in less than 25 msec (i.e., 40 Hz stimulation rate), a charge-balanced current of at least 80–100 μA is required. Since the amount of charge delivered is varied by varying the pulse duration, the output stage should be designed to deliver a constant current pulse into tissue. Thus, on-chip current regulators regulate the magnitude of the stimulus and charge-balance currents.

The microstimulator system of the present invention receives both, data and power, from an external transmitter which modulates the envelope of a radio-frequency carrier signal. The RF wave form powers the microstimulator by inducing a current in the receiver coil which charges up a hybrid capacitor for power storage and an on-chip capacitor to be used as the power source for the electronic circuitry. Control data is transferred to the microstimulator by modulating the RF carrier such that a serial bit stream "1"s and "0"s is generated and used by the microstimulator to initiate the stimulation process.

FIG. 2 is a function block diagram of the overall electronic system for the microstimulator. As shown, the RF signal is picked up by receiver coil 14 and the modulated control data is demodulated and wave-shaped by wave shaping circuitry 30. The output of wave-shaping circuitry is coupled to a control logic unit 31 which generates appropriate digital control signals to turn on output stage 32. Output stage 32 injects a charge into the tissue of the living being for a duration determined by the external transmitter (not shown in this figure). As indicated, the charge is delivered to the tissue via stimulating electrode 19 and reference electrode 18.

Figure 4:
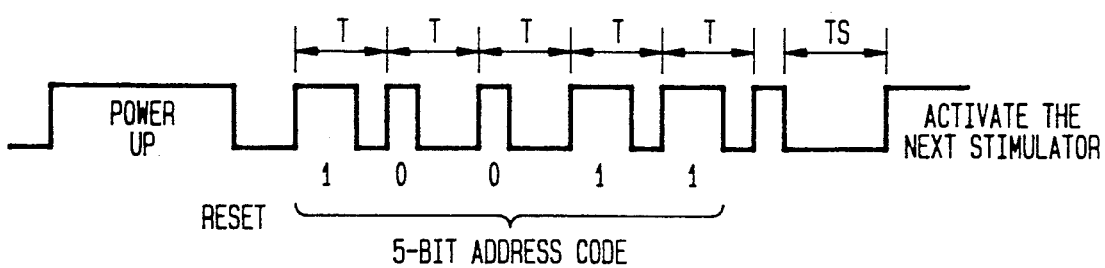
FIG. 4 is a graphical representation of power/data transmission format for a multi-receiver microstimulator telemetry link.
Figure 3:
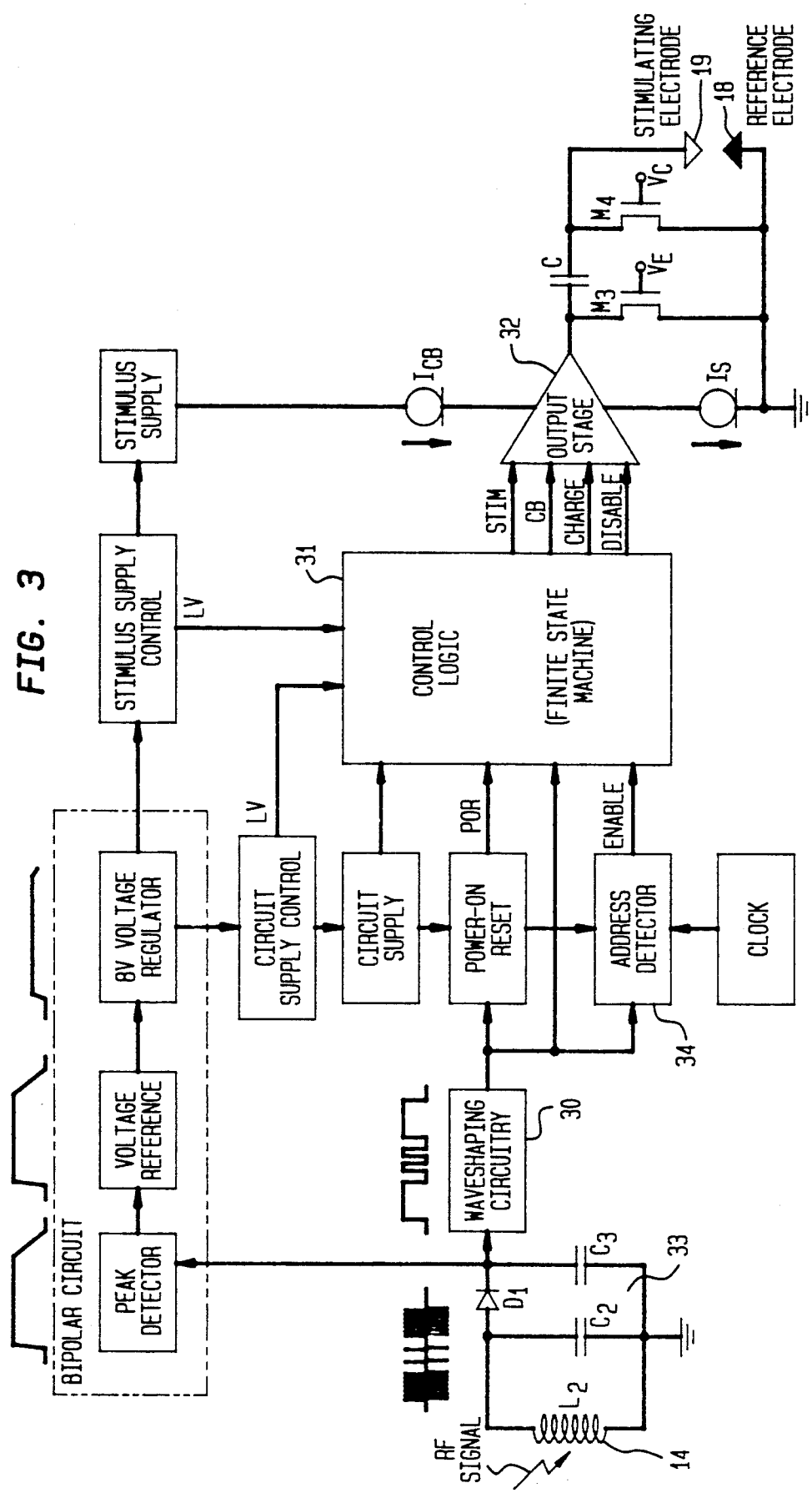
FIG. 3 is a block and line representation of the electronic system of the implantable microstimulator of FIG. 1.

FIG. 4 is a graphical representation of a pulse sequence and power/data transmission format for the transmitter-receiver telemetry link of the present invention. This system and communication format are designed for the control and operation of 32 individual microstimulators, such as microstimulator 10, using a single transmitter. Each microstimulator has a specific address which is encoded into the central electronic circuitry at the time of fabrication.

When the transmitter is initially turned on, all receivers are powered up at the same time, since all of the receiver coils (14) of the respective implantable microstimulators are tuned to the same transmission frequency by the tuning circuit which is designated generally as 33. After power-up, the transmitter is turned off. This operation resets all circuit blocks at the falling edge of the power-up pulse. All receivers will now await the receipt of a 5-digit address code from the transmitter. If the transmitted address and the address of the particular receiver match, an address detector 34 will issue an enable command to control logic unit 31, which will enable output stage 32. The output stage then awaits the receipt of a stimulus pulse command through the transmitter. After the transmission of the last address bit, the transmitter is turned on again. When the transmitter is turned off, the duration of the OFF period provides an indication of the stimulus pulse duration. Thus, the stimulator will inject charge into the tissue of the living being for the length of time the transmitter is OFF. After the stimulation period, the transmitter is turned back on. Two situations can exist at this point:

1. The transmitter immediately sends another stream of data to activate a second receiver. During this portion, the first receiver will be charging and will not respond to the transmitter until its storage capacitor is fully charged. Notice from FIG. 4 that the address pulses are short and have high repeat rates (5–10 μsec pulse widths and 15 μsec pulse periods). Therefore, the first receiver will still be able to extract sufficient energy from the RF field.

2. There is no need to activate another receiver, in which case the transmitter is kept ON to permit the storage capacitor of the first receiver to charge. At this point, all receivers are ready to be activated.

The importance of the foregoing protocol is that as far as each receiver's circuitry is concerned, it counts a predetermined number (seven in this embodiment) of falling-edges in both cases mentioned above so that the sequencing and detection of the address bits can be performed without losing count.

Figure 5:
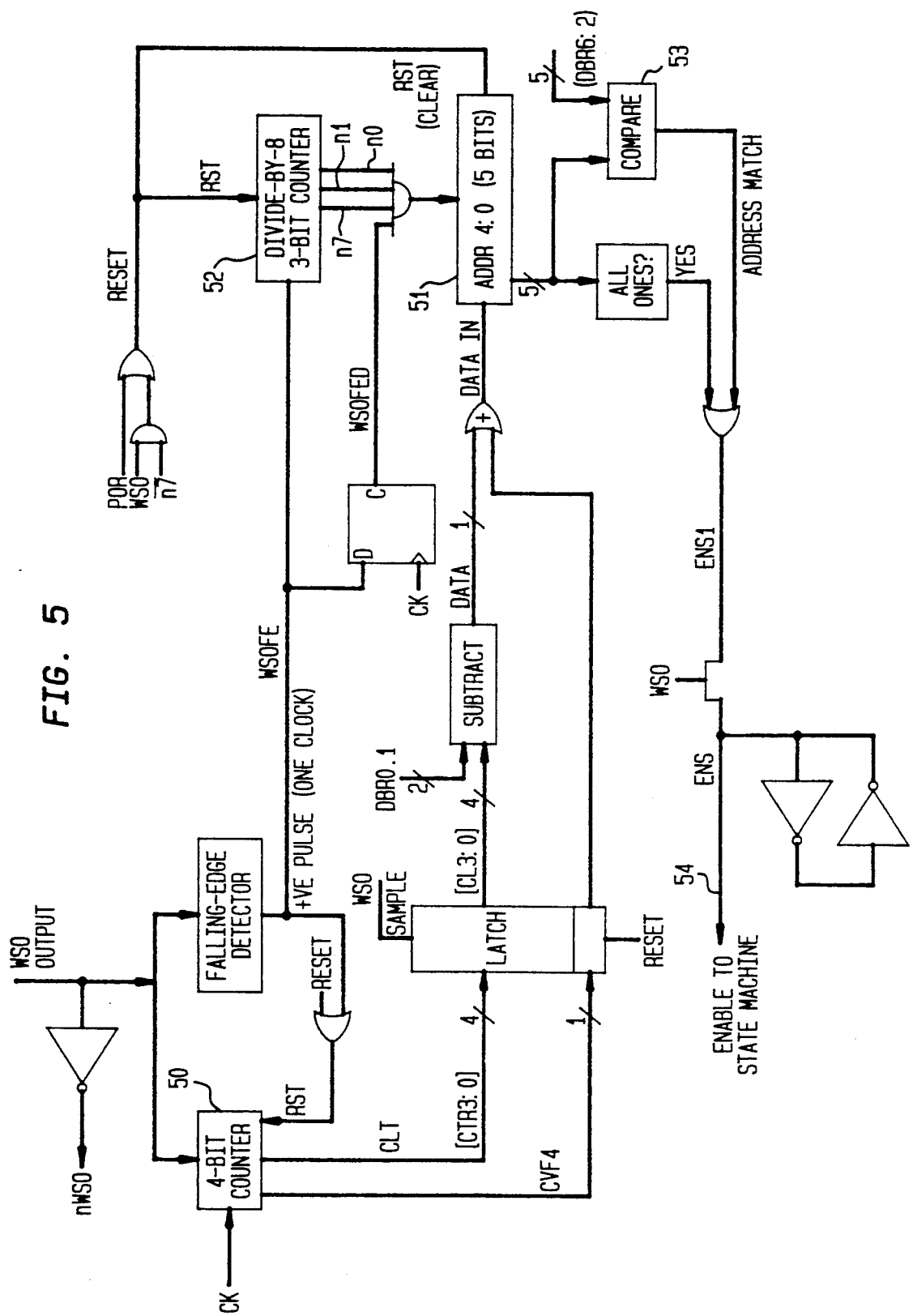
FIG. 5 is a function block representation of address detection circuitry.

FIG. 5 is a function block representation of a logic circuit designed to implement the communication protocol described hereinabove. As noted, the address of the selected stimulator is communicated by active high pulses, which are then followed by an active low pulse which defines the duration of the stimulus. The address assigned to each stimulator and some other parameters that control its operation are defined by the discretionary bonding of pads, which basically involves the shorting individual bits in a discretionary bonding register (DBR). The bits are simply bonding pads which can be shorted either to ground or VDD using wire bonding. Although this is a simple and inexpensive system for encoding each receiver with a specific address, it consumes a rather large amount of chip area. Another method for achieving the same goal is to use a laser beam to cut selective connections of the DBR bits to ground or VDD. This approach does not require the use of bond wires or large bonding pads.

As seen in FIG. 4, a "0" bit in the communicated address is differentiated from a "1" by the duration of an active high pulse. This duration is timed by a four-bit counter 50, shown in FIG. 5, which is driven by an on-chip ring oscillator (not shown). The minimum count necessary to register a "1" is programmable via discretionary bonding. Such programmability provides some flexibility in the communication protocol and also allows compensation for process-related variations in the frequency of the ring oscillator. The address bits are then sequentially shifted into a five-bit register 51 which is controlled by a three-bit counter 52. Counter 52 is initialized during power-up, and any loss of power to its logic or any violation of the communication protocol will cause it to lose count. The contents of the address shift register are then compared with the address of the stimulator at comparator 53 and used to generate an enabling window at output 54. The enabling window signal (ENS) is a key pulse from which controls for all other actions (e.g., charge balance, disable, etc.) can easily be derived using straightforward logic circuitry.

Figure 6:
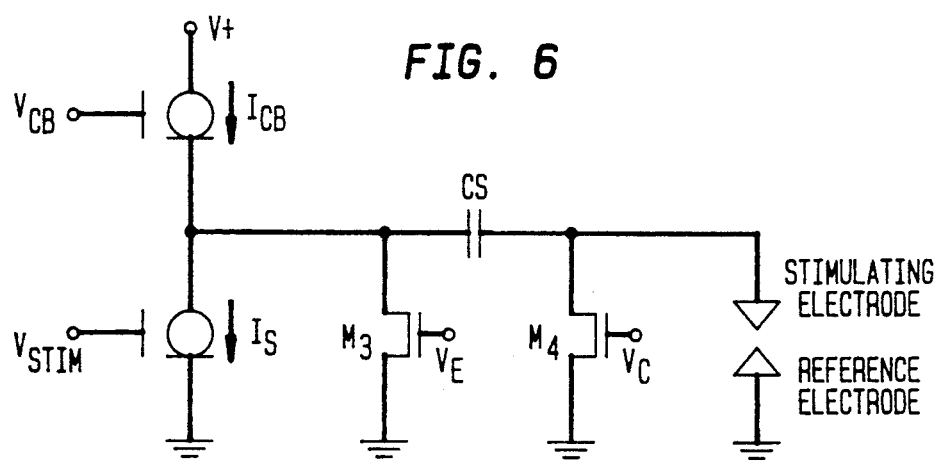
FIG. 6 is a schematic representation of the output stage of a specific illustrative embodiment of the invention for driving the stimulating and reference electrodes.

FIG. 6 is a schematic representation of a specific illustrative embodiment of an output stage which drives the stimulating and reference electrodes. The output stage provides a regulated stimulation output current $I_S$ for excitation of the tissue, and a regulated charge-balanced current $I_{CB}$, to recover the injected charge and achieve charge neutrality. When the microstimulator is initially turned on, a stimulus capacitor 60 is charged up to the supply voltage V+ through a current regulator 61. After stimulus capacitor 60 is charged, it holds its charge until the receiver receives the stimulus command from outside and initiates a stimulation period. A further current regulator 62 discharges capacitor 60, and a constant current $I_S$ will flow from reference electrode 18 through stimulating electrode 19. This will continue until the control circuitry turns the regulator off, indicating the end of the stimulation period. At this time, stimulation capacitor 60 is charged up to the supply voltage (V+) through the stimulating and reference electrodes, and the charge balance current regulator 61. This will continue until the capacitor is fully charged and the electrode tissue interface is charge balanced. The output stage then awaits receipt of the next stimulus command from the control circuitry. The placing of the charge storage capacitor 60 in series with the stimulating and reference electrodes provides a simple method for charge balance, and also decouples the stimulating electrode from the active circuitry so that no DC current flows through the stimulating electrode. Transistors 63 and 64 function as safety devices. Both of these transistors can be turned on to discharge the capacitor in the event an error is detected by the control circuitry. This will prevent the flow of any charge through the stimulating electrode.

Figure 7A:
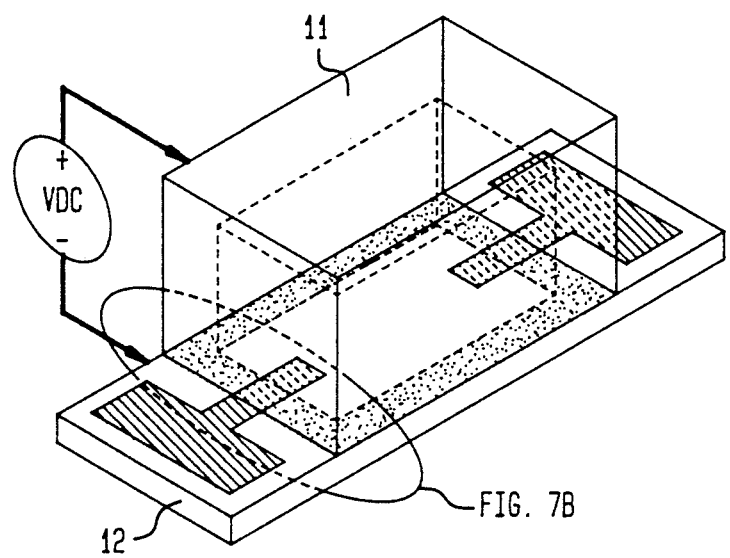
FIG. 7 is a simplified schematic isometric representation which illustrates a technique for installing a glass capsule housing on the silicon substrate of the implantable microstimulator arrangement.
Figure 7B:
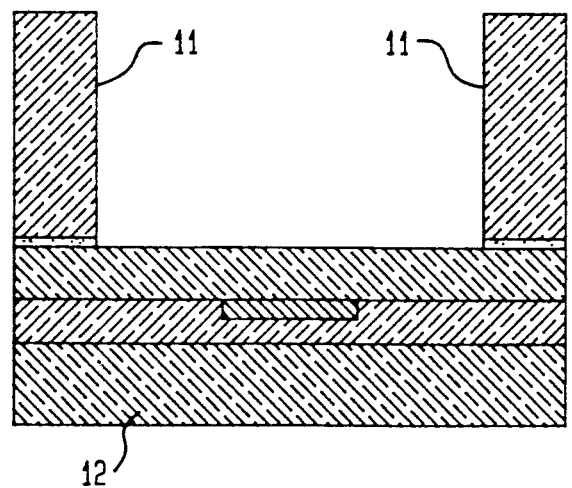

FIG. 7 is a pair of related schematic isometric and cross-sectional representations of an embodiment of the invention which is useful in illustrating certain aspects of the fabrication of the device. Fabrication begins with a silicon substrate 12 of standard thickness, arbitrary impurity, and (100) orientation. The silicon substrate is used as a support base and supports the stimulating and reference electrodes (not specifically designated in this figure). The electronic circuitry, storage capacitor, and receiver coil (not shown in this figure) are all added and connected to this substrate later. The entire structure is then encapsulated with glass capsule 11.

Fabrication of the electrodes and the silicon substrate is achieved by thermally oxidizing the silicon wafer to grow a 1.0 μm thick layer of silicon dioxide. The oxide is then patterned in the shape of the microstimulator substrate, and is removed using BHF. The wafer is then subjected to a deep bond diffusion at 1175° C. for 15 hours to create a highly boron doped region which is approximately 15 μm thick. The wafer is then stripped of all oxide. A combination of 1000 Å of silicon dioxide, 1500 Å silicon nitride, and 3000 Å silicon dioxide is then deposited using a low pressure chemical vapor deposition (LPCVD) process. The multiple dielectric layer isolates the electrode conductors from the silicon substrate. Then, the conductor metal, which can be iridium, tantalum, molybdenum, or tungsten, is deposited by sputtering or e-beam evaporation and is patterned using a lift-off process. These refractory metals are selected because of their resistance to high-temperature environments to which they will be subjected in the following process steps. The thickness of the film is made very small (less than 500 Å) in the regions where the glass capsule is to be bonded to the silicon substrate. The conductor metal is made thicker outside of the bonding regions in order to reduce the sheet resistance of the conductor. The wafer is then coated with multiple films of silicon nitride (1000 Å), silicon dioxide (4000 Å) to insulate the conductors. These dielectrics are then interconnected with the stimulator circuitry, and the exposed conductive surfaces are inlaid with iridium through a lift-off process. The iridium is then activated to create an anodized iridium oxide film which forms the stimulating surface. Iridium oxide has been chosen because of its very high charge injection capabilities.

At this point, the silicon substrate is complete and ready to be mounted with the hybrid components. These are: (1) the CMOS and bipolar integrated circuit chips that are connected to the cathode and anode electrodes already formed on the silicon substrate; (2) the tantalum chip capacitor which is used for charge storage (commercially available); (3) the solenoid coil which is used as the antenna for reception of power and control data; and (4) the custom-made glass capsule which is sealed to the silicon substrate and provides a hermetic package for the entire system.

As previously indicated, long-term operation of the implantable microstimulator, and the avoidance of damage to surrounding tissue, are insured by encapsulation of the implant in a hermetically-sealed package. Conventional packaging techniques cannot readily be applied to this device since the package must not only be biocompatible, but also must provide the necessary space for housing the receiver coil and storage capacitor. In the practice of the present invention, this has been achieved by utilizing a custom-made glass capsule which is electrostatically bonded to the silicon substrate. Referring for the moment to FIG. 1, glass capsule 11 is used as a lid which can be electrostatically bonded to silicon substrate 12, and thereby provide a hermetic package for the microstimulator components. The silicon-glass bonding is performed at temperatures of approximately 400°–450° C. using an electrostatic voltage of 800–1000 V applied across the glass-silicon combination, with silicon being the anode, as shown in FIG. 7. Due to the very small size of the microstimulator, the glass capsule has to be fabricated according to very small dimensions, and the bonding surface of the glass must be very smooth (roughness should be smaller than 500 Å) and free of any defects such that a reliable and perfect bond can be achieved to the silicon substrate. Finally, the glass should have a thermal expansion coefficient which matches closely that of silicon so that induced thermal stresses are minimized. This is considered to be very critical for reliable long-term operation of the microstimulator. Accordingly, in a practical embodiment of the invention, Corning Glass Code No. 7740 has been used for the capsules as it has a thermal expansion coefficient which matches closely that of silicon. The size specifications for the capsule are summarized hereinbelow in Table 2.

TABLE 2

| SPECIFICATIONS FOR THE GLASS CAPSULE | |
|---|---|
| Length: | 8.2 mm (OD) |
|  | 7.5 mm (ID) |
| Width: | 1.8 mm (OD) |
|  | 1.2 mm (ID) |
| Height: | 1.8 mm (OD) |
|  | 1.2 mm (ID) |
| Wall Thickness: | 0.28 mm |
| Material: | Corning COde #7740 Glass |

Figure 8:
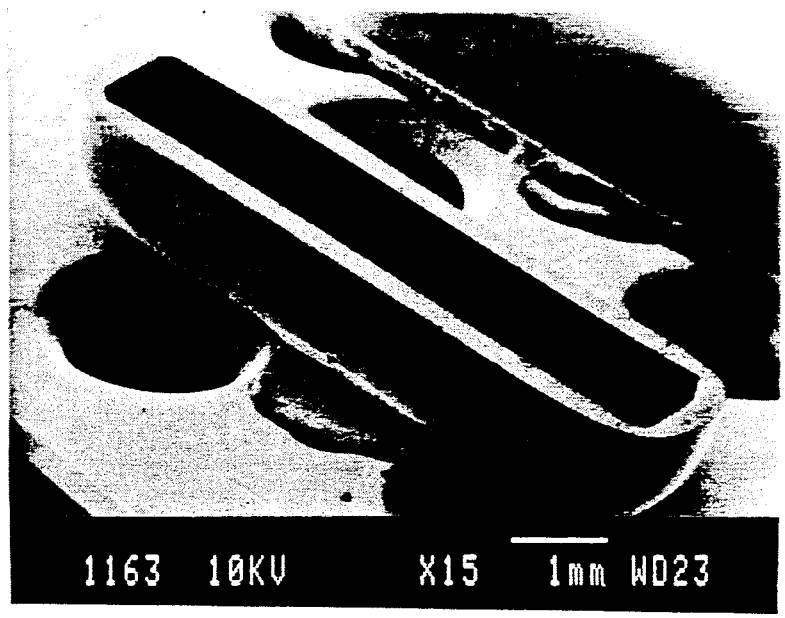
FIG. 8 is a picture of a glass capsule taken with a scanning electron microscope.

FIG. 8 is a picture showing a custom-made glass capsule taken with a scanning electron microscope (SEM). The capsule measure 1.8 by 1.8 by 8.2 mm and is fabricated such that the bonding surface between the glass and the silicon substrate is polished to result in a high quality seal. As indicated previously, electrostatic bonding is used to seal the glass hermetically to the silicon substrate.

Figure 9:
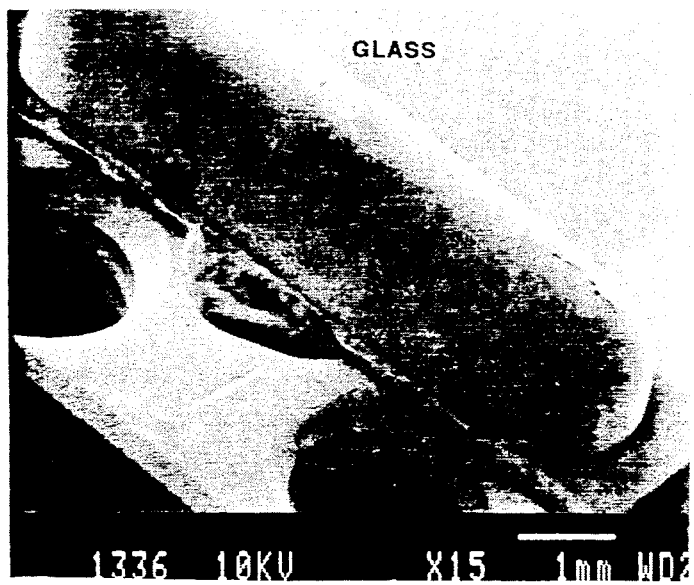
FIG. 9 is a picture of a glass capsule bonded to a silicon substrate taken with a scanning electron microscope.
Figure 10:
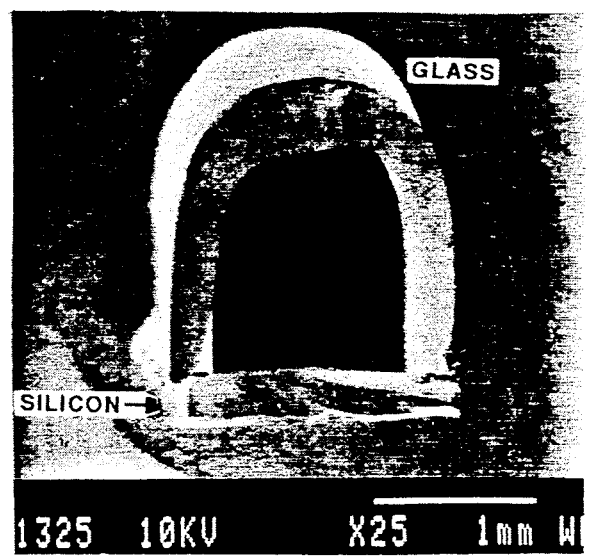
FIG. 10 is a picture of the cross-section of a cleaved glass-silicon structure taken with a scanning electron microscope.

FIG. 9 is a SEM picture which shows a capsule bonded to a silicon substrate. In FIG. 10, the glass capsule and the silicon substrate have been cleaved to show a cross-section of the bonded combination. Helium leak tests of glass capsules bonded to both bare silicon and silicon insulated with 1 $\mu$m of LPCVD silicon dioxide and silicon nitride show a leak rate lower than $5 \times 10^{-9}$ cm$^3$ per sec at a pressure of 1 atm. Since the inside volume of the capsule is approximately 10 mm$^3$, it will take about 2.5 years to penetrate completely the capsule at this rate. It is a feature of the present invention that the glass capsule is bonded only around the perimeter, thereby leaving enough space for the circuitry and the hybrid components therewithin.

It is important for any hermetically sealed device that the transfer leads into the sealed cavity not compromise the integrity of the seal. FIG. 11 shows a sequence of operations whereby a thin (less than 500 Å) metallic conductor is insulated using LPCVD dielectrics and whereby the glass capsule is bonded directly over the conductor-dielectric combination. It has been shown that electrostatic glass-silicon bonds can cover over steps less than 500 Å. In order to be able to bond successfully over the metallic conductor, the dielectric combination which insulates the conductor from the substrate and the external environment is made of a sandwich of silicon nitride and silicon dioxide.

Referring to FIG. 11, a 1000 Å layer of silicon dioxide 111, a 1500 Å layer of nitride 112, and 3000 Å layer of oxide 113 are deposited using a LPCVD process. The wafer is then patterned with photoresist 115 in the shape of the metallic conductor 116. An etching process is employed to remove approximately 500 Å of the top oxide in BHF in order to create a recess 117 in the oxide. A 500 Å thick metal is deposited using e-beam evaporation or sputtering. Metallic films which can be used for the interconnect include most of the refractory metals including iridium, tungsten, tantalum, and molybdenum. Tungsten and molybdenum are preferred since they have a thermal expansion coefficient which is closer to silicon than iridium or tantalum. The extra metal is then lifted off in the field recess using a lift-off process.

The wafer is then covered with a further layer 120 of 1000 Å of nitride, and a 3500 Å layer 121 of silicon dioxide. These LPCVD dielectric layers not only seal the conductor but also planarize the step over the metallic conductor in order to facilitate electrostatic bonding of the glass capsule over the conductor. The total dielectric thickness at this point is approximately 1 $\mu$m which is thin enough to allow electrostatic bonding of the silicon substrate and the glass capsule to be achieved.

Glass capsule 11 is then bonded to the silicon substrate across the dielectric-conductor combination as previously discussed. In order to reduce the total resistance of the interconnect, the iridium film need be thin only under the bond regions. Lead transfers into the glass chamber using this technique can be achieved without increasing the leak rate above levels mentioned hereinabove. In addition, since the interconnect is sandwiched between LPCVD dielectrics, excessive electrical leakage is prevented. Such leakage has prevented the use of diffused interconnects.

Figure 12A:
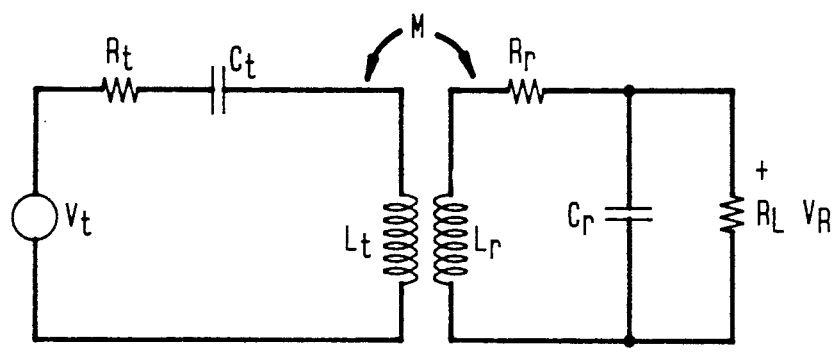
FIGS. 12A and 12B are schematic representations of the radio frequency telemetry link used in the practice of the invention.
Figure 12B:
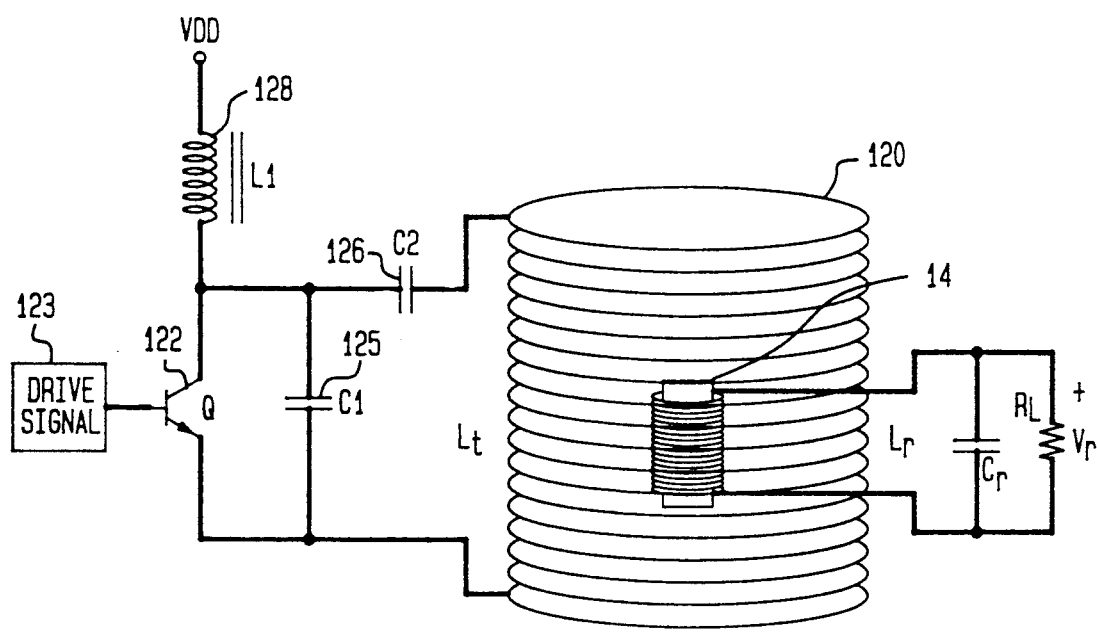

As previously indicated, one of the most challenging features of the microstimulator is the requirement for the transfer of very high power levels using a RF telemetry link. In order to achieve the power transfer levels mentioned hereinabove, the power supply must provide a minimum of 8 V, which is to be received by a coil which is less than 1.7 mm in diameter. FIG. 12 is a schematic representation of the telemetry link of the present invention. This telemetry link is based on the use of coaxial solenoid coils, one being receiver coil 14, and the other being a transmitter coil 120. As shown, the transmitter coil surrounds the receiver coil and sets up an electromagnetic field which induces sufficient power in the receiver coil. As a result of the very small size of the receiver coil, the inductive link provides for a very small mutual inductance between the coils, i.e., the coils are weakly coupled and the mutual inductance is very low. The open-circuit voltage induced at the receiver, $V_r$, for such a system is:

$$\frac{V_r}{V_t} = \frac{M}{L_t} Q_t Q_r \quad (1)$$

where $V_t$ is the transmitter voltage, M is the mutual inductance, and $Q_t$ and $Q_r$ are the quality factors of the transmitter and receiver respectively. The mutual inductance M is, in turn, given by:

$$M = \frac{\pi}{2} N_t N_r \mu \frac{Y_r^2}{Y_t} \quad (2)$$

where $N_t$ and $N_r$ are the number of turns in the transmitter and receiver coils, $\mu$ is the permeability of the receiver coil, and $Y_r$ and $Y_t$ are the diameters of the receiver and transmitter coils, respectively.

Equations (1) and (2) indicate that for a given transmitter voltage and coil parameters, it is desirable that the receiver coil have: (1) a large number of turns; (2) as large of a diameter as possible; and (3) as high a $\mu$ as possible in order to maximize the induced voltage across it. In microtelemetry systems, however, the receiver coil diameter is forced to be very small. Therefore, a coil with a large number of turns and high permeability (achieved by using ferrite cores) is needed. Equation (1) also indicates that a large transmitter voltage is desired if a high voltage amplitude is to be induced at the receiver.

It is considered important in most prostheses applications that devices operate from batteries, and the efficient use of the battery energy is an important goal in the design of the transmitter. FIG. 12 illustrates the circuit diagram of a class E power amplifier which can be used with the transmitter of the present invention. Active transistor 122 operates as a switch when driven by an appropriate signal, obtained from drive signal generator 123. The switch is operated at the fundamental resonant frequency of the load network defined by the capacitor-inductor combination of capacitors 125 and 126 and transmitter coil 120. As the switch is operated at the resonant frequency, DC energy from the power supply through a RF choke inductor 128 is converted to AC energy at the switching frequency. High efficiency is obtained by avoiding the imposition of simultaneous substantial voltage and current on the switch. This results in very low power dissipation in the active switch, ensuring that all the power is transmitted to the output coil. The basic operation of this circuitry is understandable by persons of ordinary skill in this art.

The transmitter which has been designed for a practical embodiment of the invention employs the following circuit values: $L_1 = 1.5$ mH with Q of 43 at 1 MHz; $L_2 = 136$ $\mu$H with an unloaded Q of 105 (loaded $Q_{tL}$ of approximately 20) measuring 9 cm in diameter, 7 cm long, with 41 turns; $C_1 = 2$ nF; $C_2 = 200$ pF, and a Motorola bipolar power transistor 2N 5230. This transmitter operates from a single 12 V rechargeable battery and generates 1.5 W of power at a center frequency of 1 MHz. The measured transmitter efficiency is approximately 90%. The transmitter antenna voltage reaches 150 V peak, while the peak current voltage through the transmitter is 0.3 A. The rechargeable gel-cell batteries used to operate the transmitter are rated at 1.9 Ampere-hours, and have a lifetime of approximately 6 hours at this power level. In operation, the current is nearly 0 through transistor 122 at the peak collector voltage. At the time of the peak collector current, the voltage is equal to the saturation voltage of the transistor. This results in a minimum number of components, delivering high voltage and power levels required for the present application. In addition, this circuitry provides high efficiency which is crucial in battery-operated applications.

Figure 13:
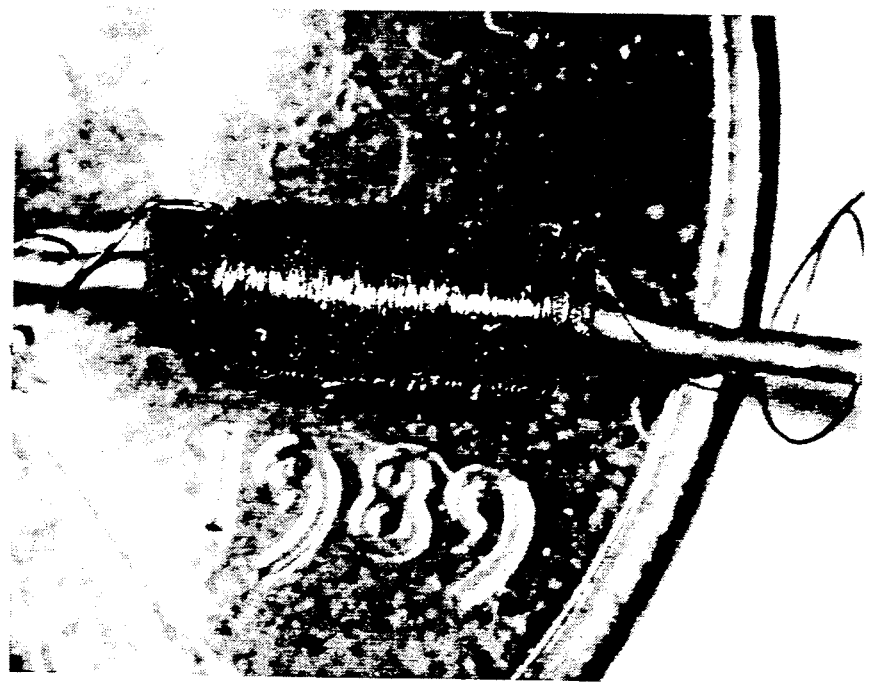
FIG. 13 is a picture of a ferrite-cired coil which is approximately 5 mm long, with a diameter of 1.5 mm, having 180 turns of 40 gauge wire.

As previously noted, the receiver coil needs to be very small, while allowing sufficient power to be generated for the on-chip electronics and stimulator. A ferrite-cored solenoid coil has been employed in a practical embodiment of the invention, and is shown in the photograph of FIG. 13. This coil is approximately 5 mm long, with a diameter of approximately 1.5 mm, including 180 turns of 40 gauge wire. This results in a total inductance of approximately 72 $\mu$H, and a Q of approximately 60 at 1 MHz. The receiver coil can pick up a peak-to-peak voltage of up to 100 V, which is rectified and regulated to generate power for the implant. As previously noted, the received power is stored in a miniature hybrid capacitor, and is sufficient to drive the electronics and deliver current into tissue for stimulation.

As in any RF powered device, it is an important requirement that the system exhibit minimum sensitivity to misalignments between the receiver and transmitter coils. The receiver coil is proportional to cos $\phi$, with $\phi$ being the misalignment angle between the two coils. The telemetry link described here is operational for misalignment angles as large as 50°. It should be noted, however, that misalignment sensitivity is a function of the received RF voltage and the desired regulated supply voltage. These requirements are summarized hereinbelow in Table 3:

TABLE 3

PERFORMANCE OF THE TRANSMITTER AND RECEIVER CIRCUITS

| PARAMETER | PERFORMANCE |
|---|---|
| Transmission Frequency | 1 MHz |
| Transmitter Supply | 12 v Battery |
| Transmitter Antenna Size | 7 cm (dia) by 9 cm long |
| Receiver Antenna Size | 1.5 mm (dia) by 5 mm long |
| Transmitted Power | 30mW across 2.3 k-ohms |
| Peak-Peak Received Voltage | 50–60 v across 8 k-ohms |
| Battery Lifetime | 6 hours |
| Transmitter Range | 4–5 cm |
| Maximum Misalignment | 50° |

Since the telemetry link described herein is based upon a double-tuned inductively-coupled system, provisions for tuning or the receiver coil should be made. The capacitance required to resonate the above coil at 1 MHz is approximately 300 pF. If slightly higher resonant frequencies are used, this capacitor can be reduced further in the range of tens of picofarads. This capacitor value can be easily achieved using on-chip MOS capacitors which will avoid the use of discrete capacitors and will allow tuning the receiver to the transmitter frequency, thereby ensuring maximum power transfer.

It is an important aspect of the present invention that control information is transmitted to and from the implant, in addition to operating power. Control signals can be superimposed on the RF carrier by modulating the carrier. In most applications, a serial stream of digital code is transmitted to either program the device, or to initiate proper actions. Digital control signals are encoded onto the carrier in the form of long and short pulses, as described hereinabove, corresponding to logical "1"s and "0"s. The transmitter switch is driven with a frequency modulated drive signal. The load network consisting of the capacitor-inductor transmits only the signal at its resonant frequency, while inhibiting transmission of the signal away from its resonant frequency. The driving of the transmitter with a FM signal is crucial in obtaining high-speed modulation of the carrier.

Figure 14A:
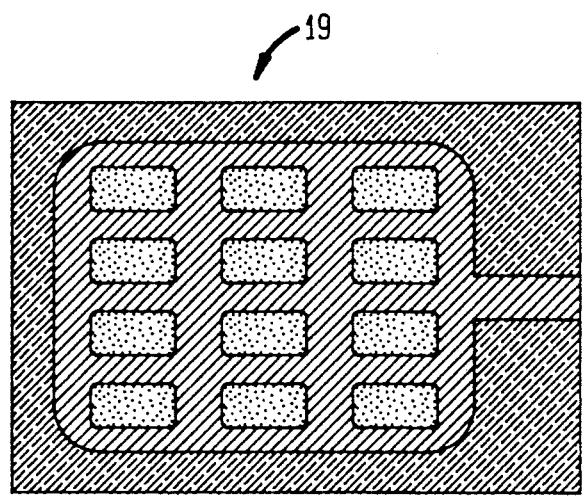
FIGS. 14A and 14B show a simplified schematic illustration of a waffle-shaped electrode designed for delivering large current pulses into tissue.
Figure 14B:
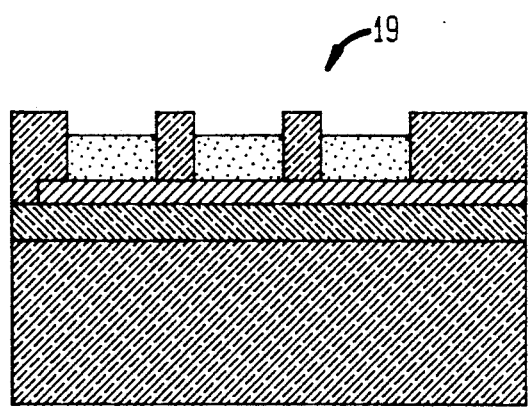

A further important requirement of the present invention is the ability to pass large amounts of current into the tissue using relatively small stimulating and reference electrodes. Most electrodes used in the past and in many systems in use today are very large wire electrodes which occupy large space and are not compatible with the sizes required for the microstimulator. The present invention employs iridium oxide as the stimulating site material, in a plurality of sites which are coupled electrically in parallel. The use of a single large stimulating electrode introduces the problem that the very large current density around the perimeter of the site results in failure due to the delamination of the electroconductor. The approach of the present invention avoids the delamination problem by increasing the total edge area. This is achieved by creating a relatively large number of openings in the top dielectric which insulates the electrode conductor from the biological environment. FIG. 14 illustrates the waffle-shaped electrode 19 of the present invention. This design, which employs a number of smaller stimulating sites, has the advantage that each site only carries a small portion of the total current, and therefore the current density at the edges of each site will be much smaller. Long-term pulse tests on 4000 $\mu m^2$ sites shows that these sites can withstand over 100,000,000 current pulses of more than 100 $\mu A$. Thus, if 4000 $\mu m^2$ sites are used, 50 of them will be required to create a 200,000 $\mu m^2$ total area, and each site will have to carry approximately 200 $\mu A$, for a total of 10 mA required for the stimulating electrode.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An electrical stimulator system for delivering a controlled electrical stimulation into the body of a living being, the system comprising:
    a non-implantable portion, said non-implantable portion being provided with:
        code generator means for producing a coded information; and
        transmitter means for transmitting an electromagnetic energy signal, said electromagnetic energy signal containing said coded information;
    an implantable portion comprising a silicon substrate upon which are provided:
        a receiver coil for receiving said electromagnetic energy signal;
        code detector means coupled to said receiver coil for detecting coded information contained in said electromagnetic energy signal;
        energy storage means coupled to said receiver coil for storing electrical energy obtained from said electromagnetic energy signal;
        a housing cover having an edge portion which is bonded to a surface of said silicon substrate to form an hermetically sealed housing with said silicon substrate, said receiver coil, said code detector means, and said energy storage means being arranged in said hermetically sealed housing;
        stimulator electrode means formed directly on said surface of said silicon substrate coupled to said energy storage means for coupling electrically with the living being, said stimulator electrode means being formed of a plurality of electrode subportions, said stimulator electrode means being arranged exterior of said hermetically sealed housing; and
        electrical coupling means for coupling said stimulator electrode means electrically to the interior of said hermetically sealed housing, said electrical coupling means comprising thin metallic conductor means interposed intermediate of said silicon substrate and said edge portion of said housing cover bonded thereto.

2. The electrical stimulator system of claim 1 wherein there is further provided reference electrode means formed directly on said silicon substrate and coupled to said energy storage means for coupling electrically with the living being.

3. The electrical stimulator system of claim 1 wherein said transmitter means comprises a transmitter coil, said transmitter coil being adapted to surround said receiver coil during transmission of said electromagnetic energy signal.

4. The electrical stimulator system of claim 1 wherein there are provided a plurality of said implantable portions and said coded information comprises address information for identifying a predetermined one of said implantable portions.

5. The electrical stimulator system of claim 1 wherein said implantable portion is further provided with demodulator means for separating said coded information in said electromagnetic energy signal from a carrier component of said electromagnetic energy signal.

6. The electrical stimulator system of claim 1 wherein said stimulator electrode means is formed of a plurality of electrode sites coupled electrically in parallel for increasing an effective length of electrode edge, whereby edge current density is maintained below a predetermined value.

7. An implantable prosthetic arrangement for delivering a stimulating electrical energy and information to the interior of the body of a living being, the implantable prosthetic arrangement comprising:
    a radio-frequency antenna in the form of a miniature receiver coil for receiving electromagnetic energy which is transformed into the electrical energy and which contains the information for controlling the delivery of the electrical energy;
    energy storage means coupled to said radio frequency antenna for storing electrical energy obtained from said electromagnetic energy signal;

a silicon substrate for supporting said radio frequency antenna and said energy storage means on a surface thereof;

a housing cover having an edge portion bonded to said silicon substrate to form an hermetically sealed housing, said radio-frequency antenna and said energy storage means coupled thereto being arranged in said hermetically sealed housing;

stimulator electrode means formed directly on said silicon substrate and coupled to said energy storage means for coupling electrically with the living being, said stimulator electrode means being formed of a plurality of electrode subportions; and coupling means for electrically coupling said stimulator electrode means to the interior of said hermetically sealed housing, said coupling means being formed of thin metallic conductor means interposed in the region where said silicon substrate and said housing cover edge portion are bonded to one another so as to extend along said surface of said silicon substrate from the interior to the outside of said hermetically sealed housing.

8. The arrangement of claim 7 wherein said miniature receiver coil is formed of approximately 180 turns of 40 gauge wire.

9. The arrangement of claim 7 wherein there is further provided a non-implantable transmitter coil for transmitting the electromagnetic energy and inducing an electrical current in said miniature receiver coil.

10. The arrangement of claim 9 wherein said transmitter coil and said miniature receiver coil are arranged substantially coaxially with respect to one another.

11. The arrangement of claim 7 wherein there is further provided demodulator means coupled electrically to said miniature receiver coil for separating an information signal component from a carrier component of a radio-frequency signal received by said miniature receiver coil.

12. The arrangement of claim 11 wherein there is further provided decoder means for deciphering the information in the information signal component, and the electrical energy stored in said energy storage means is obtained from the carrier component of the radio-frequency signal.

* * * * *